United States Patent
Kim et al.

[11] Patent Number: 5,925,728
[45] Date of Patent: Jul. 20, 1999

[54] WATER-SOLUBLE OR WATER-DISPERSIBLE POLYASPARTIC ACID DERIVATIVES, THEIR PREPARATION AND THEIR USE

[75] Inventors: Son Nguyen Kim, Hemsbach; Axel Sanner, Frankenthal; Peter Hössel, Schifferstadt; Matthias Kroner, Eisenberg, all of Germany

[73] Assignee: BASF Aktiengesellschaft, Ludwigshafen, Germany

[21] Appl. No.: 08/886,294

[22] Filed: Jul. 1, 1997

[30] Foreign Application Priority Data

Aug. 2, 1996 [DE] Germany ............... 196 31 380

[51] Int. Cl.$^6$ ............... C08G 69/10; C08G 73/06
[52] U.S. Cl. ............... 528/328; 528/360; 528/361; 528/363; 525/418; 525/419; 525/420
[58] Field of Search ............... 528/328, 360, 528/363, 361; 525/418–420

[56] References Cited

U.S. PATENT DOCUMENTS

| | | | |
|---|---|---|---|
| 3,846,380 | 11/1974 | Fujimoto et al. | 528/328 |
| 4,735,797 | 4/1988 | Grollier et al. | 424/47 |
| 4,745,161 | 5/1988 | Saudek et al. | 525/420 |
| 5,175,285 | 12/1992 | Lehmann et al. | 544/141 |
| 5,328,631 | 7/1994 | Du Yosel et al. | 252/174.23 |

FOREIGN PATENT DOCUMENTS

| | | |
|---|---|---|
| 767 191 | 4/1997 | European Pat. Off. . |
| 2424292 | 11/1979 | France . |
| 2005705 | 4/1979 | United Kingdom . |

OTHER PUBLICATIONS

Neuse et al., *Die Ange. Makromol. Chem.*, vol. 192, No. 3300, 1991, pp. 35–50.

Derwent Abstracts, Sectin Ch, Week 9440, An 94–322255 (English abstract of JP 6248072A, Sep. 6, 1994).

*Primary Examiner*—P. Hampton-Hightower
*Attorney, Agent, or Firm*—Keil & Weinkauf

[57] ABSTRACT

A description is given of water-soluble or water-dispersible polyaspartic acid derivatives, their preparation and their use in cosmetology, especially in hair cosmetology.

10 Claims, No Drawings

WATER-SOLUBLE OR WATER-DISPERSIBLE POLYASPARTIC ACID DERIVATIVES, THEIR PREPARATION AND THEIR USE

FIELD OF THE INVENTION

The present invention relates to water-soluble or water-dispersible polyaspartic acid derivatives, to their preparation and to their use in cosmetology.

BACKGROUND OF THE INVENTION

Synthetically produced polyamino acids and their derivatives have been known for a long time and on the basis of their biological compatibility are used, for example, for specific applications in medicine and pharmacy. Apart from peptides having an effect-specific sequence, such compounds are principally film-forming substances for improving the handling properties of pharmaceutical preparations, for improving their storage stability and, in particular, for influencing the rate of release of the active substances. For these applications use is made, for example, of polymers of individual amino acids, such as polyaspartic acid, polyglutamic acid and polylysine, and also of copolymers and biologically readily compatible derivatives of such polyamino acids.

DE-A-37 00 128 describes poly(hydroxyalkyl) aminodicarboxylic acid derivatives having biologically inactive acyl groups, processes for their preparation and their use for depot preparations with controlled release of active substance.

DE-A-36 12 102 describes soluble and biodegradable copolymers comprising aspartic and/or glutamic acid units and containing reactive groups, for example hydrazide or azide groups, for the chemical attachment of biologically active substances.

EP-B-0 406 623 describes film-forming polyaspartic acid derivatives which are obtained by reacting polysuccinimide with amines and comprise structural units of the formula

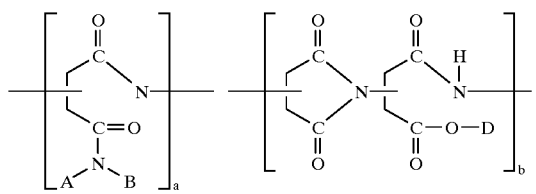

where
A=H or alkyl or alkylene of 1 to 8 carbons which can also be branched and can in addition be substituted by cycloaliphatic or aromatic radicals, it also being possible for the cyclic substituent to contain heteroatoms, or by R—O groups, where R=H or linear or branched alkyl or cycloalkyl of 1 to 10 carbons,
B=H or alkyl or alkylene as defined under A, which can be the same as or different from A,
D=H or NH$_4$ or

where A and B are as defined above, or an alkali, and
a=0.2 to 1 and
b=0.8 to 0, which are used as coating materials and/or retardants for drug forms of therapeutic active substances and for foods and tobacco products. As the above formula shows, the monomer units, which are in salt form, are always attached to an imide monomer unit. The stoichiometric ratio of monomer units in salt form to imide monomer units is fixed at 1:1.

The cosmetic use of polyamino acids and their derivatives has also been described before. Polypeptides of protein hydrolysates, based for example on albumen or collagen, are obtainable commercially. For example, protein hydrolysates or partial hydrolysates of collagen with a molar weight of from 1100 to 1300 and from about 8 to 14 monomer units and their sodium salts (eg. Nutrilan® from Grünau) are used as protective colloids which do not foam and are not active in washing but which have dispersing and soil transport properties, for example in combination with surfactants. Similarly, various fatty acid-polypeptide condensation products are obtainable commercially as biodegradable anionic surfactants having good foaming and washing properties (eg. Lamepon® from Grünau).

DE-A-22 53 190 describes polyaspartic acid derivatives having acid amide radicals and alkali metal carboxylate and/or alkaline earth metal carboxylate radicals, their preparation by reacting polysuccinimide having a molecular weight of from 300 to 30,000 with a primary or secondary amine and then hydrolyzing the product with alkali metal or alkaline earth metal hydroxide or carbonate, and the use of the resulting products as surfactants and additives for detergents and cosmetics.

JP-A-0624 8072 describes the cosmetic use of polyaspartamides having alkali metal carboxylate radicals.

In the field of cosmetology there is a great demand for water-soluble or -dispersible polymers with good biocompatibility, biodegradability and film-forming properties. Such film-forming polymers are used, for example, to strengthen, shape and improve the structure of hair. The hair treatment compositions generally comprise a solution of the film former in alcohol or in a mixture of alcohol and water and are sprayed in the form, for example, of these aqueous-alcoholic solutions onto the hair. Following the evaporation of the solvent, the hair is held in the desired shape at the points of mutual contact of the polymer which remains. The polymers should on the one hand be sufficiently hydrophilic that they can be washed out of the hair, but on the other hand should be hydrophobic, so that hair treated with the polymers retains its shape even under conditions of high atmospheric humidity and the individual hairs do not stick to one another. To maximize the hairsetting effect it is desirable, moreover, to employ polymers having a relatively high molecular weight (K value>14 in accordance with E. Fikentscher, Cellulosechemie 13 (1932), pp. 58–64). However, because of their high molecular weight these polymers are generally more difficult to wash out.

The use of the above-described polymers based on polyamino acid derivatives in cosmetology for strengthening, shaping and improving the structure of hair has not been described hitherto. Moreover, the known polymers do not fulfill the requirement of having good setting properties while nevertheless being easy to wash out.

BRIEF SUMMARY OF THE INVENTION

It is an object of the present invention, therefore, to provide polymers which are based on polyamino acid derivatives and which on the one hand can be used as hairsetting agents but which, on the other hand, also have improved washing-out properties (redispersibility).

We have found that this object is achieved, surprisingly, by water-soluble or water-dispersible polyaspartic acid derivatives which are products of the reaction of polysuccinimide or polyaspartic acid with an amine mixture which in general comprises at least one short-chain amine and at least one longer-chain amine.

DETAILED DESCRIPTION OF THE INVENTION

The present invention provides water-soluble and/or water-dispersible polyaspartic acid derivatives on the basis of the units shown in the diagrammatic formula I

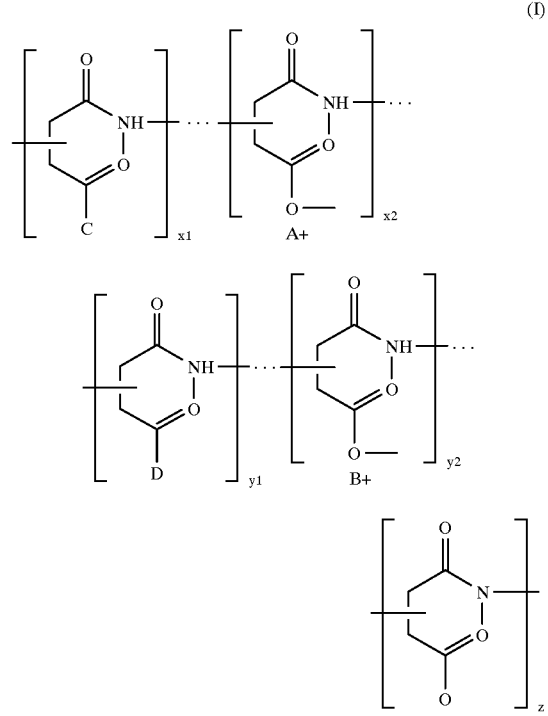

(I)

where
the sequence of the units is arbitrary,
the sum of x1+x2+y1+y2+z=is 100, and
x1+x2 is 30–99.9,
y1+y2 is 0.1–70 and
z is 0–20,
A is at least one primary, secondary or tertiary alkylamine having 2 to 6 carbons per alkyl, and the alkyls can be substituted by 1, 2 or 3 groups selected independently from hydroxyl and alkoxy, and/or A is at least one diamine of the formula II

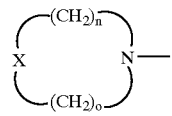

(II)

where
m is an integer from 2 to 6,
$R^1$ and $R^4$ can be identical or different and are hydrogen or alkyl,
$R^2$ and $R^3$ can be identical or different and are alkyl, or $R^2$ and $R^3$, together with the nitrogen to which they are attached, are a 5- to 7-membered saturated heterocycle of the formula III

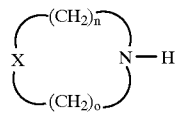

(III)

where
n and o can be identical or different and are an integer from 1 to 5,
X is $CH_2$, S, O, $NR^5$ or $NCOR^5$, and
$R^5$ is H or alkyl,
and/or A is at least one cyclic diamine of the formula IIIa,

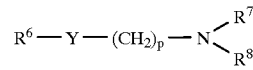

(IIIa)

where
n and o are as defined above,
X is $NR_5$, and
$R^5$ is H or alkyl,
B is at least one amine of the formula IV

(IV)

where $R^6$—Y—$(CH_2)_p$ has 6 to 24 carbons,
p is an integer from 1 to 23,
Y is $CH_2$, O, NH, CONH where the CO is attached to $R^6$, or

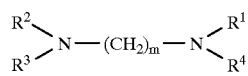

$R^6$ is hydrogen or the hydrocarbon radical of a saturated or unsaturated fatty acid,
$R^7$ and $R^8$ can be identical or different and are hydrogen, alkyl, hydroxyalkyl or —[$CH_2$—$CH_2$—O—$]_r$H,
where
r is an integer from 1 to 30, and
$R^9$ is alkyl,
C is a radical which is derived from an amine of type A having primary or secondary amino groups by elimination of an amine hydrogen,
D is a radical which is derived from an amine of type B having primary or secondary amino groups by elimination of an amine hydrogen,
where at least one of the amines A and B has a tertiary amino group;
or their carboxylic acid salts and polycarboxylic acid salts or quaternization products.

For the purposes of the present invention the term alkyl covers straight-chain or branched alkyl, preferably $C_1$–$C_{30}$-alkyl. Alkyl is preferably straight-chain or branched $C_1$–$C_8$- alkyl, particularly preferably $C_1$–$C_6$-alkyl and, in particular, $C_1$–$C_4$-alkyl. Particular examples of alkyl are methyl, ethyl, propyl, 1-methylethyl, butyl, 1-methylpropyl, 2-methylpropyl, 1,1-dimethylethyl, n-pentyl, n-hexyl and ethylhexyl.

Hydrocarbon radicals derived from a naturally occurring, saturated or unsaturated fatty acid are then, for example, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, n-eicosyl, n-docosyl, 9-hexadecenyl, 9-octadecenyl or 13-docosenyl, 2,4-hexadienyl and 9,12-octadienyl.

Examples of suitable radicals of the formula III are pyrrolidine, piperidine, azepan, imidazolidine, N-alkylimidazolidine, N-acylimidazolidine, oxazolidine, morpholine, piperazine, N-alkylpiperazine, N-acylpiperazine, etc.

The radical C is derived from a primary or secondary amine of type A from which an amine hydrogen has been eliminated in a condensation reaction to form an amide bond.

The radical D is derived from a primary or secondary amine of type B from which an amine hydrogen has been eliminated in a condensation reaction to form an amide bond.

The radical $A^+$ is derived from an amine of type A which has formed an ammonium salt with a carboxyl group.

The radical $B^+$ is derived from an amine of type B which has formed an ammonium salt with a carboxyl group.

The terminal groups of the polymers are radicals having two free terminal carboxyls or one free terminal amino and one free carboxyl and, if desired, their partial or complete quaternization products or, if desired, their salts with amines of the type A or B or, if desired, their salts with carboxylic or polycarboxylic acids which are used for neutralization.

If A is a primary, secondary or tertiary alkylamine of 2 to 6 carbons it is preferably a primary or tertiary amine.

In one preferred embodiment A is a tertiary alkylamine where one of the alkyls is substituted by hydroxyl or alkoxy.

In that case A is, for example, N,N-dimethylethanolamine, N,N-dimethylpropanolamine or, in particular, N,N-diethylethanolamine.

A is preferably, furthermore, a diamine of the formula II having one primary and one tertiary amino, where $R^1$ and $R^4$ are hydrogen and $R^2$ and $R^3$ can be identical or different and are short-chain alkyl.

In that case A is, for example, N,N-dimethylethylenediamine, N,N-dimethyl-1,4-butanediamine, N,N-dimethyl-1,5-pentanediamine, N,N-diethylethylenediamine, N,N-diethylpropylenediamine, etc., and especially N,N-dimethylpropylenediamine.

In a further preferred embodiment A is a diamine of the formula II having one primary and one tertiary amino, where $R^1$ and $R^4$ are hydrogen and $R^2$ and $R^3$, together with the nitrogen to which they are attached, are a 5- to 7-membered saturated heterocycle of the formula III where X is $CH_2$ or O.

In that case A is, for example, N-(β-aminoethyl) pyrrolidine, N-(3-aminopropyl)pyrrolidine or morpholinoethylamine.

In a further preferred embodiment A is a saturated heterocycle of the formula IIIa where X is $NR^5$ and $R^5$ is hydrogen or alkyl. In that case A is, for example, N-methylpiperazine, N-ethylpiperazine or N-propylpiperazine.

B is preferably an amine of the formula IV where Y is $CH_2$ and $R^7$ and $R^8$ are hydrogen.

In that case B is, for example, 1-hexylamine, 1-heptylamine, 1-octylamine, 1-nonylamine, 1-decylamine, 1-undecylamine, 1-undec-10-enylamine, 1-tridecylamine, 1-tetradecylamine, 1-pentadecylamine, 1-hexadecylamine, 1-heptadecylamine, 1-octadecylamine, 1-octadeca-9,12-dienylamine, 1-nonadecylamine, 1-eicosylamine, 1-eicos-9-enylamine, 1-heneicosylamine, 1-docosylamine and, in particular, 1-dodecylamine or amine mixtures prepared from naturally occurring fatty acids, for example tallow fatty amines, which contain predominantly saturated and unsaturated $C_{14}$-, $C_{16}$- and $C_{18}$-alkylamines, or coconut amines, which contain saturated, monounsaturated and diunsaturated $C_6$–$C_{22}$-, preferably $C_{12}$–$C_{14}$-alkylamines. Examples of suitable amine mixtures are Armeen® grades from AKZO Chemie or Noram® grades from Ceca.

In a further preferred embodiment the novel polyaspartic acid derivatives include, as amine or amine mixture of type B, tertiary fatty amines of the formula IV, where Y is $CH_2$ and $R^7$ and $R^8$ can be identical or different and are alkyl, especially relatively short-chain alkyls.

In that case B is, for example, N,N-dimethyl-1-hexylamine, N,N-diethylhexylamine, etc. In particular, B is dialkylated tallow fatty amines, dialkylated hydrogenated tallow fatty amines and dialkylated coconut amines, and is especially a mixture of N,N-dimethyl-$C_{12}$–$C_{14}$-alkylamines. Examples of suitable amines are Noram® DM from Ceca.

In a further preferred embodiment the novel polyaspartic acid derivatives include, as amine or amine mixture of type B, hydroxyethylated or ethoxylated fatty amines of the formula IV where Y is $CH_2$ and $R^7$ and $R^8$ can be identical or different and are alkyl or $-\!\!+\!\!CH_2\!\!-\!\!CH_2\!\!-\!\!O\!\!+\!\!_r\!H$ where r is an integer from 1 to 30. Examples of suitable amines are Noramox® from Ceca and especially Noramox O5, an ethoxylated oleylamine with 5 ethylene oxide units.

In a further preferred embodiment the novel polyaspartic acid derivatives include, as amine or amine mixture of type B, a fatty amine of the formula IV in which Y is CONH.

In a further preferred embodiment the novel polyaspartic acid derivatives include, as amine or amine mixture of type B, a diamine of the formula IV in which Y is NH and $R^7$ and $R^8$ are hydrogen.

In that case $R^6$ is, in particular, a relatively long-chain alkyl and B is, for example, N-oleyl-1,3-diaminopropane, N-dodecyl-1,3-diaminopropane or N-alkylated 1,3-diaminopropanes with alkyls derived from tallow fatty acids or coconut fatty acids. Examples of suitable amines are Dinoram® grades from Ceca, Duomeen® grades from Akzo and the types 6540, 6560, 6570 and 6572 from Fina.

The novel water-soluble or water-dispersible polyaspartic acid derivatives are, in particular, derivatives of the diagrammatic formula I where x1+x2 is 50–97, y1+y2 is 3–50, and z is 0–15.

The molar proportion of quaternary ammonium groups in the polyaspartic acid derivatives in the formula I, expressed as the sum x2+y2, is preferably 50% or more, especially 70% or more. These derivatives are readily biodegradable.

In a particularly preferred embodiment the novel polyaspartic acid derivatives are derivatives of the formula I where x1 and y1 are 0.

The derivatives involved are, specifically, those where

A is at least one tertiary amine having 2 to 6 carbons and/or is a diamine of the formula II

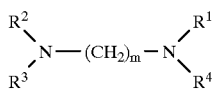

where
- $R^1$ and $R^4$ can be identical or different and are alkyl and $R^2$, $R^3$, $R^5$, X, m, n and o are as defined above for the preferred embodiments, and
- B is at least one tertiary amine of the formula IV, in particular a tertiary amine, in which the substituents are as defined for the preferred embodiments.

The novel polyaspartic acid derivatives are prepared by reacting polyaspartic acid or polysuccinimide with at least one amine of type A and at least one amine of type B in water as solvent. If polysuccinimide is used to prepare the novel polyaspartic acid derivatives, it is preferably prepared by polycondensation of aspartic acid to give high molecular mass polysuccinimide with molecular weights of up to 100,000. The preparation takes place by known methods, for example by polycondensation in the presence of phosphoric acid as described, for example, by P. Neri et al in J. Med. Chem. 16, (1973) 893.

To prepare the polyaspartic acid derivatives the polysuccinimide or the polyaspartic acid is placed in water at, for example, from 20 to 70° C. An amine mixture containing one amine of each of types A and B described above is added with stirring. The reaction is allowed to proceed, expediently under nitrogen and at from 30 to 100° C., preferably from 50 to 80° C., until the imide structure is virtually no longer detectable by IR spectroscopy. If desired, the temperature can also be raised and/or excess amine can be removed (for example by distillation). The product can subsequently either be quaternized with a quaternizing agent, for example dimethyl sulfate, or neutralized with an acid or a polycarboxylic acid, for example lactic acid or polyaspartic acid, respectively.

The proportion of added amines is preferably as great as or greater than is required by the stoichiometry of the reaction with the monomer units of the polyaspartic acid or of the polysuccinimide. Water-insoluble amines can preferably be employed already in neutralized form.

To obtain polymers having good conditioning properties it is necessary for both amines of type A and amines of type B to be present in the polymer in the abovementioned amounts, preferably in salt form, in order to achieve good biodegradability at the same time. In the abovementioned, particularly preferred embodiment the polymer no longer contains any amide groups. The proportions of amide units, salt units and imide units in the polymer can be controlled by way of the reaction conditions.

The novel water-dispersible compounds can be employed in the form of aqueous microdispersions having particle diameters of usually from 5 to 100 nm, in particular from 10 to 80 nm, and solids content of usually from 0.1 to 40% by weight, in particular from 3 to 30% by weight. In general, these microdispersions can be stabilized without the need for emulsifiers or surfactants.

Because of their ionic groups the polyaspartic acid derivatives are, in general, readily soluble in water and alcohol or can at least be dispersed in alcohol and water without the aid of emulsifiers. Charged groups can be produced from the existing tertiary amine nitrogen atoms either by protonation, for example with alkylating agents such as $C_1$–$C_4$-alkyl halides or $C_1$–$C_4$-alkyl sulfates. Examples of such alkylating agents are ethyl chloride, ethyl bromide, methyl chloride, methyl bromide, dimethyl sulfate and diethyl sulfate.

In addition the polyaspartic acid derivatives can also, as mentioned, be converted, by reaction with a mono- or polybasic carboxylic acid, for example lactic, citric or tartaric acid, etc., or by reaction with a polycarboxylic acid, for example polyaspartic, polyglutamic or polyacrylic acid or carboxymethylcellulose, etc., into readily water- or alcohol-soluble or dispersible salts.

The novel polyaspartic acid derivatives are useful as auxiliaries in cosmetology and pharmacy and as coating materials for the textile, paper, printing and adhesive industries. They are particularly useful in hair cosmetology and pass readily onto the hair. For use as hairsetting agents preference is given to polyaspartic acid derivatives whose K value (in accordance with Fikentscher, Cellulose Chemie 13 (1932), pp. 58–64), is from 15 to 90, in particular from 25 to 50. In addition, the polymers can also be used in creams.

The present invention also provides hair treatment compositions comprising the novel polyaspartic acid derivatives. In general the composition comprises the polyaspartic acid derivatives in an amount of from about 0.1 to 30% by weight, based on the overall weight of the composition.

The novel hair treatment compositions are usually in the form of an aqueous dispersion or an aqueous-alcoholic solution. Examples of suitable alcohols are ethanol, propanol, isopropanol, etc. The compositions then comprise the polyaspartic acid derivative in an amount of from about 0.1 to 25% by weight, preferably from 1 to 15% by weight.

The novel hair treatment compositions can also, in general, comprise customary cosmetic auxiliaries, for example plasticizers, such as glycerol and glycol, silicones, emollients, fragrances, UV absorbers, colorants, thickeners, antistats, combability improvers, preservatives and foam stabilizers.

If desired, the hair treatment compositions additionally comprise at least one conventional hairsetting polymer. The proportion by weight of polyaspartic acid derivative to the other hairsetting polymer is in this case, in particular, from 1:0.1 to 1:2. The hair treatment composition contains the polymer mixture in an amount of from 0.1 to 25% by weight, preferably from 1 to 15% by weight.

If the novel compositions are formulated as hairspray they comprise a sufficient amount of a propellant, for example a low-boiling hydrocarbon or ether, such as propane, butane, isobutane or dimethyl ether. Other propellants which can be used are compressed gases such as nitrogen, air or carbon dioxide. The amount of propellant is kept as low as possible so as not to bring about an unnecessary increase in the VOC (volatile organic compounds) content. In general it is not more than 40% by weight, based on the overall weight of the composition.

The novel polyaspartic acid derivatives and compositions comprising them have the advantage that on the one hand they give the hair the desired strength and on the other hand the polymers are easier to wash out (more redispersible) than the prior art polymers. Furthermore, it is possible to prepare hair treatment compositions having a VOC content of less than 60% by weight and even purely aqueous formulations, even if they are formulated as hairsprays.

The intention of the nonlimiting examples given below is to illustrate the invention:

EXAMPLES a) Preparing the polyaspartic acid derivatives

Preparation Example 1:

97 g of polysuccinimide and 26.7 g (0.2 mol) of $C_{12}$–$C_{14}$-dimethyl amine in 400 g of water are charged to a threenecked flask fitted with stirrer, dropping funnel and reflux condenser and are stirred under nitrogen at 60 to 70° C. for 16 hours. The pH of the solution is then adjusted to 9.2 and 96.4 g (0.83 mol) of diethylethanolamine are slowly added dropwise. The reaction mixture is then stirred at about 90° C. until imide structures are virtually absent from the IR spectrum. At 110° C. the excess amine is distilled off together with the water, to give a solution of the polyaspartic acid derivative with a strength of about 40%.

Examples 2 to 6 in Table 1 below were prepared by a similar method.

TABLE 1

| Example No. | Si. mol | $C_{12/14}$-DMA mol | Noram.O5 mol | $C_{12}$-A mol | DEEA mol | DMPDA mol |
|---|---|---|---|---|---|---|
| 1 | 1 | 0.1 | — | — | 0.9 | — |
| 2 | 1 | 0.2 | — | — | 0.83 | — |
| 3 | 1 | — | 0.2 | — | 0.83 | — |
| 4 | 1 | — | 0.2 | — | — | 0.5 |
| 5 | 1 | — | — | 0.1 | — | 0.42 |
| 6 | 1 | — | — | 0.3 | 0.75 | — |

Si.: succinimide units in the polymer
$C_{12/14}$-DMA: $C_{12}$—$C_{14}$-dimethylamine
Noram.O5: Noramox ® O5 (ethoxylated oleylamine with 5 EO units from CECA)
$C_{12}$-A: dodecylamine
DEEA: diethylethanolamine
DMPDA: N,N-dimethylpropylenediamine b) Biodegradability The biodegradability was determined by the OECD test specifications OECD 302 B (Zahn-Wellens test) and OECD 301 B (Sturm test). The former determines the degree of oxidative degradation by the amount of $CO_2$ liberated within a defined period (60 days), while the latter determines the eliminability of the substance itself. The results of the analysis are given in Table 2.

TABLE 2

| | Biodegradability | |
|---|---|---|
| Ex. No. from Table 1 | Amount of $CO_2$ [%] | Eliminability [%] |
| 1 | 92% (60 d) | >93% |
| 2 | 87% (60 d) | >90% |
| 3 | 90% (60 d) | >95% |
| 4 | 82% (60 d) | >85% |
| 5 | 85% (60 d) | >90% |
| 6 | 87% (60 d) | >90% | c) Use examples

In order to demonstrate the use of the novel polyaspartic acid derivatives as hair conditioner polymers the following polymer solutions and polymer/surfactant solutions were prepared and then the wet combability of strands of hair treated with them was determined:

| A) Polymer solution: | |
|---|---|
| Polymer 1–6 from Table 1 | 1% by weight |
| Preservative based on benzyl alcohol/isothiazolone | 0.1% by weight |
| Water | 98.9% by weight |
| B) Polymer/surfactant solution: | |
| Polymer 1–6 from Table 1 | 1% by weight |

| | |
|---|---|
| Texapon ® NSO (ethoxylated nonylphenol sulfonate from Henkel KgaA) | 10% by weight |
| Preservative based on benzyl alcohol/isothiazolone | 0.1% by weight |
| Water | 88.9% by weight |

Wet combability after washing off the polymer solution with hand-hot drinking water:

Each strand of hair was immersed for 30 minutes in the following solutions:

| | |
|---|---|
| 100 g | of deionized water (= blank value for polymer solutions A) |
| 100 g | of 1% strength Luviquat ® FC 370 (copolymer of vinylpyrrolidone and vinylimidazole quaternized with dimethyl sulfate, from BASF AG) |
| 100 g | of test polymer solutions A) |

Wet combability after washing off the polymer/surfactant solution with hand-hot drinking water:

Each strand of hair was immersed completely for 30 minutes in the following solutions:

| | |
|---|---|
| 100 g | of 10% strength Texapon ® NSO (= blank value for polymer solutions B) |
| 100 g | of 1% Luviquat ® FC 370 in a surfactant solution (10% strength Texapon ® NSO) |
| 100 g | of test polymer/surfactant solutions B) |

After gently wiping off the hair between the fingers, the strands are each rinsed for one minute under hand-hot drinking water (30–40° C.). Using a fine-toothed comb from Hercules (tooth spacing 1 mm) the strands are combed in a climatically controlled chamber and assessed: all polymer solutions A) and polymer/surfactant solutions B) of Examples 1 to 6 from Table 1 exhibit conditioning properties which were at least as good as those of Luviquat® FC 370.

We claim:

1. A water-soluble or water-dispersible polyaspartic acid derivative on the basis of the units shown in the diagrammatic formula I

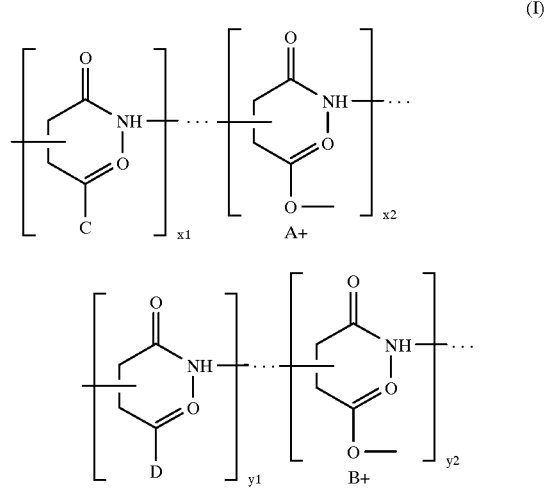

-continued

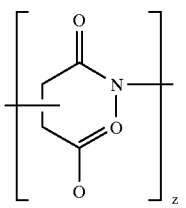

where the sequence of the units is arbitrary,
the sum of x1+x2+y1+y2+z=is 100, and
x1+x2 is 30–99.9,
y1+y2 is 0.1–70 and
z is 0–20,
A+ is derived from amine A which has formed an ammonium salt with a carboxyl groups said amine A being selected independently in each occurrence from the group consisting of primary, secondary, or tertiary alkylamines having 2 to 6 carbons per alkyl, and the alkyls can be substituted by 1, 2 or 3 groups selected independently from hydroxyl and alkoxy,
and cyclic diamines of the formula IIIa,

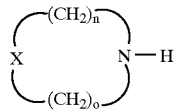 (IIIa)

where n and o can be identical or different and each is an integer from 1 to 5,
x is $NR^5$, and
$R^5$ is H or alkyl,
B+ is derived from amine B which has formed an ammonium salt with a carboxyl group, said amine B being selected independently in each occurrence from the group consisting of amines of the formula IV

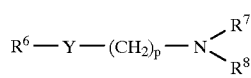 (IV)

where $R^6$—Y—$(CH_2)_p$ has 6 to 24 carbons,
P is an integer from 1 to 23,

Y is $CH_2$, O, CONH where the CO is attached to $R^6$, or

$R^6$ is hydrogen or the hydrocarbon radical of a saturated or unsaturated fatty acid,
$R^7$ and $R^8$ can be identical or different and are hydrogen, alkyl, hydroxyalkyl or —[$CH_2$—$CH_2$—O—]$_r$H,
where
r is an integer from 1 to 30, and
$R^9$ is alkyl,
C is a radical which is derived from amine A having primary or secondary amino groups by elimination of an amine hydrogen,
D is a radical which is derived from amino B having primary or secondary amino groups by elimination of an amine hydrogen,
where at least one of the amines A and B has a tertiary amino group;
or one of its carboxylic acid salts and polycarboxylic acid salts or quaternization products.

2. A polyaspartic acid derivative as claimed in claim 1, where
x1+x2 is 50–97,
y1+y2 is 3–50, and
x is 0–15.

3. A polyaspartic acid derivative as claimed in claim 1, where the sum x2+y2 is 50 or more.

4. A polyaspartic acid derivative as claimed in claim 1, wherein x1 and y1 in the formula I are 0.

5. A polyaspartic acid derivative as claimed in claim 1, where
A is at least one tertiary alkylamine having 2 to 6 carbon atoms, where the alkyls can be substituted by 1, 2 or 3 groups selected independently from hydroxyl and alkoxy, and
B is at least one tertiary amine of the formula IV.

6. A polyaspartic acid derivative as claimed in claim 1, whose K value is from 15 to 90.

7. A process for preparing a polyaspartic acid derivative as claimed in claim 1, which comprises reacting polyaspartic acid or polysuccinimide with at least one amine A and at least one amine B.

8. A process as claimed in claim 7, wherein the amines A and B are used in at least stoichiometric amounts.

9. A polyaspartic acid derivative as claimed in claim 1, where the sum of x2 and y2 is at least 70.

10. A polyaspartic acid derivative as claimed in claim 1 which has a K value of from 25 to 50.

* * * * *